(12) United States Patent
Pluta et al.

(10) Patent No.: US 9,307,935 B2
(45) Date of Patent: Apr. 12, 2016

(54) NON-INVASIVE MONITORING OF BLOOD METABOLITE LEVELS

(75) Inventors: Sarah E. Pluta, Scotia, NY (US); John W. Hewitt, Scotia, NY (US)

(73) Assignee: BioSensors, Inc., Schenectady, NY (US)

( * ) Notice: Subject to any disclaimer, the term of this patent is extended or adjusted under 35 U.S.C. 154(b) by 1159 days.

(21) Appl. No.: 13/377,162

(22) PCT Filed: Jun. 4, 2010

(86) PCT No.: PCT/US2010/037361
§ 371 (c)(1),
(2), (4) Date: Jan. 10, 2012

(87) PCT Pub. No.: WO2010/144313
PCT Pub. Date: Dec. 16, 2010

(65) Prior Publication Data
US 2012/0130212 A1      May 24, 2012

(51) Int. Cl.
*A61B 5/1468* (2006.01)
*A61B 5/145* (2006.01)
(Continued)

(52) U.S. Cl.
CPC ........... *A61B 5/14532* (2013.01); *A61B 5/0531* (2013.01); *A61B 5/14546* (2013.01); *A61B 5/1495* (2013.01); *A61B 2562/0209* (2013.01); *A61B 2562/046* (2013.01)

(58) Field of Classification Search
CPC ... A61B 5/14532; A61B 5/0531; A61B 5/053
USPC ................................. 600/345, 347, 365, 316
See application file for complete search history.

(56) References Cited

U.S. PATENT DOCUMENTS

| 4,160,447 | A | * | 7/1979 | Teshima et al. ............... 600/548 |
| 4,494,554 | A | * | 1/1985 | Van Dyke et al. ............ 600/547 |
| 5,890,489 | A |   | 4/1999 | Elden |

(Continued)

FOREIGN PATENT DOCUMENTS

| CN | 1997311 A | 7/2007 |
| CN | 101026997 A | 8/2007 |

(Continued)

OTHER PUBLICATIONS

"Wheatstone Bridge" Wikipedia, The Free Encyclopedia. Wikimedia Foundation, inc 24, Nov. 2014.*

(Continued)

*Primary Examiner* — Patricia Mallari
*Assistant Examiner* — Michael Catina
(74) *Attorney, Agent, or Firm* — Hoffman Warnick LLC

(57) ABSTRACT

Solutions for non-invasively monitoring blood metabolite levels of a patient are disclosed. In one embodiment, the method includes: repeatedly measuring a plurality of electromagnetic impedance readings with a sensor array from: an epidermis layer of a patient and one of a dermis layer or a subcutaneous layer of the patient, until a difference between the readings exceeds a threshold; calculating an impedance value representing the difference using an equivalent circuit model and individual adjustment factor data representative of a physiological characteristic of the patient; and determining a blood metabolite level of the patient from the impedance value and a blood metabolite level algorithm, the blood metabolite level algorithm including blood metabolite level data versus electromagnetic impedance data value correspondence of the patient.

19 Claims, 14 Drawing Sheets

(51) Int. Cl.
*A61B 5/053* (2006.01)
*A61B 5/1495* (2006.01)

(56) References Cited

U.S. PATENT DOCUMENTS

| | | | |
|---|---|---|---|
| 6,339,722 | B1 | 1/2002 | Heethaar et al. |
| 6,517,482 | B1 | 2/2003 | Elden et al. |
| 6,560,481 | B1 | 5/2003 | Heethaar et al. |
| 6,714,814 | B2 | 3/2004 | Yamada et al. |
| 7,184,810 | B2 | 2/2007 | Caduff et al. |
| 7,184,820 | B2 | 2/2007 | Jersey-Willuhn et al. |
| 7,315,767 | B2 | 1/2008 | Caduff et al. |
| 7,395,104 | B2 | 7/2008 | Mouradian et al. |
| 7,419,487 | B2 | 9/2008 | Johnson et al. |
| 7,534,208 | B2 | 5/2009 | Caduff et al. |
| 7,693,561 | B2 | 4/2010 | Schrepfer et al. |
| 2002/0040193 | A1 | 4/2002 | Hirschman |
| 2003/0004431 | A1 | 1/2003 | Pinyayev |
| 2003/0163061 | A1 | 8/2003 | Miyoshi et al. |
| 2003/0220581 | A1 | 11/2003 | Ollmar et al. |
| 2004/0065158 | A1 | 4/2004 | Schrepfer et al. |
| 2004/0127780 | A1 | 7/2004 | Ollmar et al. |
| 2004/0167418 | A1 | 8/2004 | Nguyen et al. |
| 2005/0177062 | A1 | 8/2005 | Skrabal et al. |
| 2005/0203363 | A1 | 9/2005 | Caduff et al. |
| 2007/0060802 | A1 | 3/2007 | Ghevondian et al. |
| 2007/0135729 | A1 | 6/2007 | Ollmar et al. |
| 2007/0161881 | A1* | 7/2007 | Ollmar et al. ............ 600/347 |
| 2007/0182417 | A1 | 8/2007 | Giaever et al. |
| 2007/0265512 | A1 | 11/2007 | Ollmar et al. |
| 2008/0057526 | A1 | 3/2008 | Caduff et al. |
| 2009/0270756 | A1 | 10/2009 | Gamache et al. |
| 2010/0099960 | A1 | 4/2010 | Caduff et al. |
| 2010/0130833 | A1 | 5/2010 | Mott et al. |
| 2011/0087129 | A1* | 4/2011 | Chetham et al. ............ 600/547 |

FOREIGN PATENT DOCUMENTS

| | | |
|---|---|---|
| RU | 2187797 C2 | 8/2002 |
| RU | 2209430 C2 | 7/2003 |
| RU | 2371707 C2 | 10/2009 |
| WO | 2005053526 A1 | 6/2005 |
| WO | 2007053526 A1 | 5/2007 |
| WO | 2007053963 A1 | 5/2007 |
| WO | WO 2007053963 A1 * | 5/2007 |
| WO | 2007075091 A2 | 7/2007 |
| WO | 2007075410 A2 | 7/2007 |
| WO | 2008141306 A2 | 11/2008 |
| WO | 2010062495 A2 | 6/2010 |
| WO | 2010144313 A3 | 12/2010 |

OTHER PUBLICATIONS

International Application No. PCT/US2010/037361, International Preliminary Report on Patentability dated Dec. 22, 2011.
Chinese Patent Application No. 201080031334.5, Office Action dated Apr. 1, 2014.
Chinese Patent Application No. 201080031334.5, Office Action dated Aug. 15, 2013.
European Patent Application No. 10786601., Extended European Search Report dated Mar. 12, 2014.
Japanese Patent Application No. P2012-515001, Notice of Reasons for Rejection dated Mar. 24, 2014.
Russian Patent Application No. 2011153773 Office Action dated Mar. 20, 2014.
Mengke, Application No. CN 201080031334.5, Notification of the First Office Action, Mar. 5, 2013, 13 pages.
Russian Patent Application No. 2011153773, Decision to Grant dated Jul. 14, 2014.
Australian Patent Application No. 2010259071, Office Action dated Jun. 11, 2014.
Australian Patent Application No. 2010259071, Notice of Acceptance dated Jul. 10, 2014.
International Application No. PCT/US2009/061247, International Search Report and Written Opinion dated May 20, 2010.
International Application No. PCT/US2009/061247, Article 34 Amendment filed Aug. 20, 2010.
International Application No. PCT/US2009061247, filed Oct. 20, 2009, International Preliminary Report on Patentability dated May 12, 2011.
International Application No. PCT/US2010037361, filed Jun. 4, 2010, International Search Report and Written Opinion of the International Searching Authority dated Dec. 8, 2010.
Tura et al., "Dielectric Properties of Water and Blood Samples With Glucose at Different Concentrations," Medicon 2007, IFMBE Proceedings 16, pp. 194-197, 2007.
Smith, John L., "The Pursuit of Noninvasive Glucose: Hunting the Deceitful Turkey," Internet Self-Publication, Copyright 2006.
Weinzimer, Stuart Alan, M.D., "PENDRA: The Once and Future Noninvasive Continuous Glucose Monitoring Device," Diabetes Technology and Therapeutics, vol. 6, No. 4, 2004.
U.S. Appl. No. 12/258,509, filed Oct. 27, 2008, Office Action dated Oct. 27, 2011.
U.S. Appl. No. 12/258,509, filed Oct. 27, 2008, Office Action dated May 4, 2011.
Aberg et al., "Minimally Invasive Electrical Impedance Spectroscopy of Skin Exemplified by Skin Cancer Assessments", IEEE, 2003.
Barker, R.D., "Depth of Investigation of Collinear Symmetrical Four-Electrode Arrays", Geophysics, vol. 54, No. 8, Aug. 1989.
Beetner, et al., Differentiation Among Basal Cell Carcinoma, Benign Lesions, and Normal Skin Using Electrical Impedance, IEEE Transactions on Biomedical Engineering, vol. 50, No. 8, Aug. 2003.
Min et al., Electrical Impedance and Cardiac Monitoring—Technology, Potential, and Applications, International Journal of Bioelectromagnetism, vol. 5, No. 1, pp. 53-56, 2003.
Parkes et al., A New Consensus Error Grid to Evaluate the Clinical Significance of Inaccuracies in the Measurement of Blood Glucose, Diabetes Care, vol. 23, No. 8, Aug. 2000.

* cited by examiner

| Electrode / Pattern | 1 | 2 | 3 | 4 | 5 | 6 | 7 | 8 |
|---|---|---|---|---|---|---|---|---|
| A |   |   | A | A | N | B |   |   |
| B |   | A | A | M | N | B | B |   |
| C | A | A | M | M | N |   |   | B |
| D |   | A | M | M | N | B |   |   |
| E |   | A |   | M | N | N |   | B |
| F |   | A | M |   |   | N | B |   |
| G | A | A | M |   |   | N | B | B |
| H | A | M | M |   |   | N | B | B |
| J | A | M |   |   |   |   | N | B |

FIG. 11

|       | \|Z\| (ohms) | Phase (degrees) |
|-------|-------------|-----------------|
| $Z_A$ | 90.03       | 0.03            |
| $Z_E$ | 127.5       | -0.28           |
| $Z_1$ | 180.06      | 0.03            |
| $Z_2$ | 437.09      | -1.03           |

FIG. 13

NON-INVASIVE MONITORING OF BLOOD METABOLITE LEVELS

CROSS-REFERENCE TO RELATED APPLICATIONS

This application is related in part to United States utility patent application Ser. No. 12/258,509, filed on 27 Oct. 2008, and U.S. provisional patent application No. 61/185,258, filed on 9 Jun. 2009, which are hereby incorporated by reference.

BACKGROUND

The present disclosure relates to non-invasive monitoring of blood metabolite levels of a patient. More specifically, the present disclosure relates to solutions for non-invasively monitoring blood metabolite levels of a patient using a sensor array and electromagnetic impedance tomography.

Blood metabolite levels, including glucose, lactic acid and hydration levels, are important indicators of health and the physical condition of a patient. In non-invasive blood-metabolite monitoring systems, measurements of biological data are taken at the surface (epidermis) of a patient's body. These surface measurements are more sensitive to changes in the body than those invasive measurements taken at the layers below (e.g., dermis or subcutaneous layers). Fluctuations in temperature, perspiration, moisture level, etc., can cause rapid and dramatic variations in a patient's biological data. When attempting to determine biological data (i.e., blood metabolite levels) through the epidermis layer (using sensors on the skin), difficulties arise in compensating for these variations.

SUMMARY

Solutions are disclosed that enable non-invasive monitoring of blood metabolite levels of a patient. In one embodiment, a method includes repeatedly measuring a plurality of electromagnetic impedance readings with a sensor array from: an epidermis layer of a patient and one of a dermis layer or a subcutaneous layer of the patient, until a difference between the readings exceeds a threshold; calculating an impedance value representing the difference using an equivalent circuit model and individual adjustment factor data representative of a physiological characteristic of the patient; and determining a blood metabolite level of the patient from the impedance value and a blood metabolite level algorithm, the blood metabolite level algorithm including blood metabolite level data versus electromagnetic impedance data value correspondence of the patient.

A first aspect of the invention provides a method comprising: repeatedly measuring a plurality of electromagnetic impedance readings with a sensor array from: an epidermis layer of a patient and one of a dermis layer or a subcutaneous layer of the patient, until a difference between the readings exceeds a threshold; calculating an impedance value representing the difference using an equivalent circuit model and individual adjustment factor data representative of a physiological characteristic of the patient; and determining a blood metabolite level of the patient from the impedance value and a blood metabolite level algorithm, the blood metabolite level algorithm including blood metabolite level data versus electromagnetic impedance data value correspondence of the patient.

A second aspect of the invention provides a blood metabolite level monitoring system comprising: a sensor array for repeatedly measuring a plurality of electromagnetic impedance readings from: an epidermis layer of a patient and one of a dermis layer or a subcutaneous layer of the patient, until a difference between the readings exceeds a threshold; a calculator for calculating an impedance value representing the difference, the calculator including an equivalent circuit model and individual adjustment factor data representative of a physiological characteristic of the patient; and a determinator for determining a blood metabolite level of the patient from the impedance value and a blood metabolite level algorithm.

A third aspect of the invention provides a program product stored on a computer readable medium, which when executed, performs the following: obtains a plurality of electromagnetic impedance readings about: an epidermis layer of a patient and one of a dermis layer or a subcutaneous layer of the patient; analyzes the electromagnetic impedance readings to determine a difference; calculates an impedance value representing the difference using an equivalent circuit model and individual adjustment factor data representative of a physiological characteristic of the patient; and determines a blood metabolite level of the patient from the impedance value and a blood metabolite level algorithm, the blood metabolite level algorithm including blood metabolite level data versus electromagnetic impedance data value correspondence of the patient.

A fourth aspect of the invention provides a blood metabolite monitoring system comprising: a device that determines a blood metabolite level of a patient based on a plurality of electromagnetic impedance readings measured from the patient within a single blood metabolite cycle of the patient.

A fifth aspect of the invention provides a method for monitoring a blood metabolite level of a patient, the method comprising: determining a blood metabolite level of a patient based on a plurality of electromagnetic impedance readings measured from the patient within a single blood metabolite cycle of the patient.

A sixth aspect of the invention provides a program product stored on a computer readable medium, which when executed, performs the following: determines a blood metabolite level of a patient based on a plurality of electromagnetic impedance readings collected from the patient within a single blood metabolite cycle of the patient.

A seventh aspect of the invention provides a blood metabolite monitoring system comprising: a signal generator for transmitting an electromagnetic signal; a sensor array for: receiving the electromagnetic signal from the signal generator and applying the electromagnetic signal to a patient; and non-invasively measuring a plurality of electromagnetic impedance readings from: an epidermis layer of the patient and one of a dermis layer or a subcutaneous layer of the patient; a comparator for comparing a difference between the plurality of electromagnetic impedance readings to a threshold; and a controller for controlling the signal generator and the comparator, the controller providing instructions for repeating the transmitting, non-invasively measuring, and comparing in response to the difference being less than the threshold.

An eight aspect of the invention provides a program product stored on a computer readable medium, which when executed, performs the following: transmits an electromagnetic signal to a sensor array; receives a plurality of electromagnetic impedance readings from the sensor array, the electromagnetic impedance readings being collected from: an epidermis layer of the patient and one of a dermis layer or a subcutaneous layer of the patient; compares a difference between the plurality of electromagnetic impedance readings to a threshold; and provides instructions for repeating the transmitting, receiving, and comparing in response to the difference being less than the threshold.

A ninth aspect of the invention provides a method for monitoring a blood metabolite level of a patient, the method comprising: transmitting an electromagnetic signal to a sensor array; receiving a plurality of electromagnetic impedance readings from the sensor array, the electromagnetic impedance readings collected from: an epidermis layer of the patient and one of a dermis layer or a subcutaneous layer of the patient; comparing a difference between the plurality of electromagnetic impedance readings to a threshold; and repeating the transmitting, receiving, and comparing in response to the difference being less than the threshold.

BRIEF DESCRIPTION OF THE DRAWINGS

These and other features of this invention will be more readily understood from the following detailed description of the various aspects of the invention taken in conjunction with the accompanying drawings that depict various embodiments of the invention, in which:

FIG. 11 shows a table including test patterns used according to embodiments of the invention.

FIG. 13 shows a table including electromagnetic impedance values obtained during testing according to embodiments of the invention.

It is noted that the drawings of the invention are not to scale. The drawings are intended to depict only typical aspects of the invention, and therefore should not be considered as limiting the scope of the invention. In the drawings, like numbering represents like elements between the drawings.

DETAILED DESCRIPTION

Shown and described herein are solutions for non-invasively monitoring blood metabolite levels of a patient. It is understood that blood metabolite level information may be used to determine a plurality of physical conditions of a patient. While other blood metabolite levels such as hydration levels and lactic acid levels may be monitored using the solutions described herein, glucose levels are used as the primary illustrative example. It is understood that these solutions may be easily adapted, with undue experimentation, to monitor hydration levels, lactic acid levels, etc. of a patient. For example, the glucose monitoring system 106, glucose determinator 126 and glucose monitor 140 shown in FIG. 1 and described herein, may alternatively be configured to monitor, i.e., hydration and/or lactic acid levels of a patient.

Figure 1:
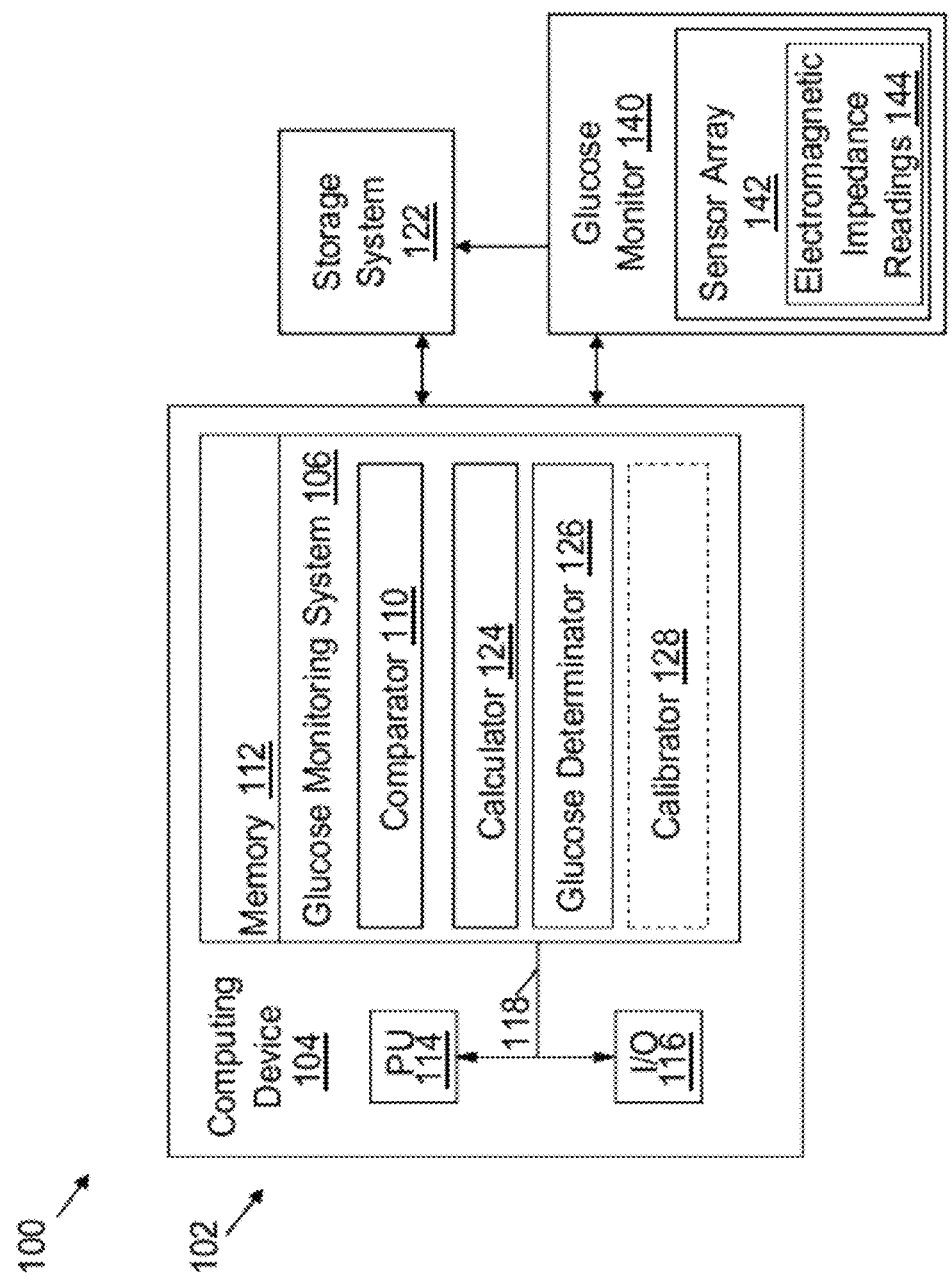
FIG. 1 shows a block diagram of an illustrative environment and computer infrastructure for implementing one embodiment of the invention.

Turning to the drawings, FIG. 1 shows an illustrative environment 100 for monitoring a glucose level of a patient. To this extent, environment 100 includes a computer infrastructure 102 that can perform the various processes described herein. In particular, computer infrastructure 102 is shown including a computing device 104 that comprises a glucose monitoring system 106, which enables computing device 104 to enable monitoring a glucose level of a patient by performing the steps of the disclosure.

Computing device 104 is shown including a memory 112, a processor unit (PU) 114, an input/output (I/O) interface 116, and a bus 118. Further, computing device 104 is shown in communication with a glucose monitor 140 and a storage system 122. In general, processor unit 114 executes computer program code, such as glucose monitoring system 106, which is stored in memory 112 and/or storage system 122. While executing computer program code, processor unit 114 can read and/or write data, such as electromagnetic impedance readings 144, to/from memory 112, storage system 122, and/or I/O interface 116. Bus 118 provides a communications link between each of the components in computing device 104.

In any event, computing device 104 can comprise any general purpose computing article of manufacture capable of executing computer program code installed by a user (e.g., a personal computer, server, handheld device, etc.). However, it is understood that computing device 104 and glucose monitoring system 106 are only representative of various possible equivalent computing devices that may perform the various process steps of the invention. To this extent, in other embodiments, computing device 104 can comprise any specific purpose computing article of manufacture comprising hardware and/or computer program code for performing specific functions, any computing article of manufacture that comprises a combination of specific purpose and general purpose hardware/software, or the like. In each case, the program code and/or hardware can be created using standard programming and engineering techniques, respectively.

Similarly, computer infrastructure 102 is only illustrative of various types of computer infrastructures for implementing the invention. For example, in one embodiment, computer infrastructure 102 comprises two or more computing devices (e.g., a server cluster) that communicate over any type of wired and/or wireless communications link, such as a network, a shared memory, or the like, to perform the various process steps of the invention. When the communications link comprises a network, the network can comprise any combination of one or more types of networks (e.g., the Internet, a wide area network, a local area network, a virtual private network, etc.). Regardless, communications between the computing devices may utilize any combination of various types of transmission techniques.

As previously mentioned and discussed further below, glucose monitoring system 106 enables computing infrastructure 102 to determine a glucose level of a patient. To this extent, glucose monitoring system 106 is shown including a comparator 110, a calculator 124, a determinator 126 and optionally, a calibrator 128. Also shown in FIG. 1 is glucose monitor 140, which may include a sensor array 142. Sensor array 142 may obtain electromagnetic impedance readings 144 from a patient, which may be, for example, a human being. Glucose monitor 140 may transmit electromagnetic impedance readings 144 to glucose monitoring system 106 and/or storage system 122. Operation of each of these components is discussed further herein. However, it is understood that some of the various functions shown in FIG. 1 can be implemented independently, combined, and/or stored in memory for one or more separate computing devices that are included in computer infrastructure 102. Further, it is understood that some of the systems and/or functionality may not be implemented, or additional systems and/or functionality may be included as part of environment 100.

Figure 2:
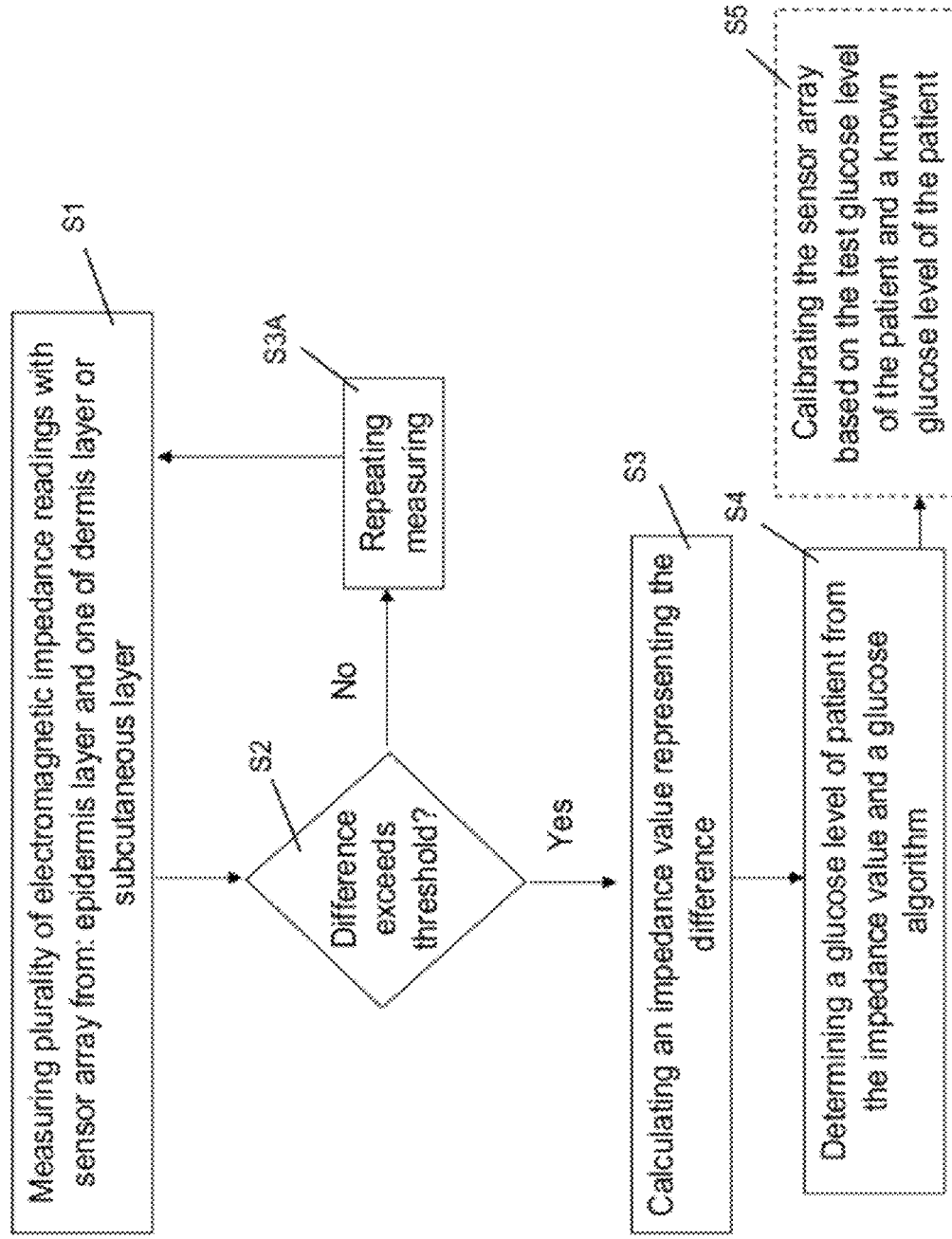
FIG. 2 shows a flow diagram of steps in monitoring a glucose level of a patient according to embodiments of the invention.

Turning to FIG. 2, and with continuing reference to FIG. 1, embodiments of a method for monitoring a glucose level of a patient will now be described. In step S1, sensor array 142 repeatedly measures a plurality of electromagnetic impedance readings 144 from an epidermis layer and one of a dermis or a subcutaneous layer of a patient until a difference between the readings exceeds a threshold. Electromagnetic impedance readings 144 may include data gathered by measuring the impedance (or "complex" impedance) of a body part of a patient to an electromagnetic signal, such as, for example, an alternating current signal. Electromagnetic impedance readings 144 may include impedance spectral data, which may be obtained by measuring the impedance of a body part of a patient across a range of frequencies. The range of frequencies may, for example be between 100 Hz and 10 MHz. In one embodiment, the range of frequencies may be between 100 kHz and 10 MHz. It is understood that frequency ranges may be controlled by, for example, a signal generator which may send electromagnetic signals to sensor array 142. In this case, signal generator may be a component in glucose monitoring system 106, glucose monitor 140, or a separate component altogether. It is further understood that electromagnetic impedance readings 144 (e.g., potential differences) may be measured by a signal analyzer. For example, electromagnetic impedance readings may be measured by an impedance analyzer, which may be a component in glucose monitoring system 106, glucose monitor 140, or a separate component altogether.

Returning to FIG. 2, step S1 may include two parts: 1) measuring a plurality of electromagnetic impedance readings 144 from an epidermis layer of a patient with sensor array 142; and 2) measuring a plurality of electromagnetic impedance readings 144 from one of a dermis layer or a subcutaneous layer of the patient with sensor array 142. It is understood that plurality of electromagnetic impedance readings 144 from one of a dermis layer or a subcutaneous layer of the patient necessarily include data about the epidermis layer of the patient. As all readings 144 described herein are obtained at the surface (epidermis layer) of a patient's skin, such readings will always include some data about the epidermis layer. For example, a reading 144 "from" or "about" the subcutaneous layer of a patient includes electromagnetic impedance data about the subcutaneous layer, the dermis layer (above the subcutaneous), and the epidermis layer (above the dermis layer).

Figure 3:
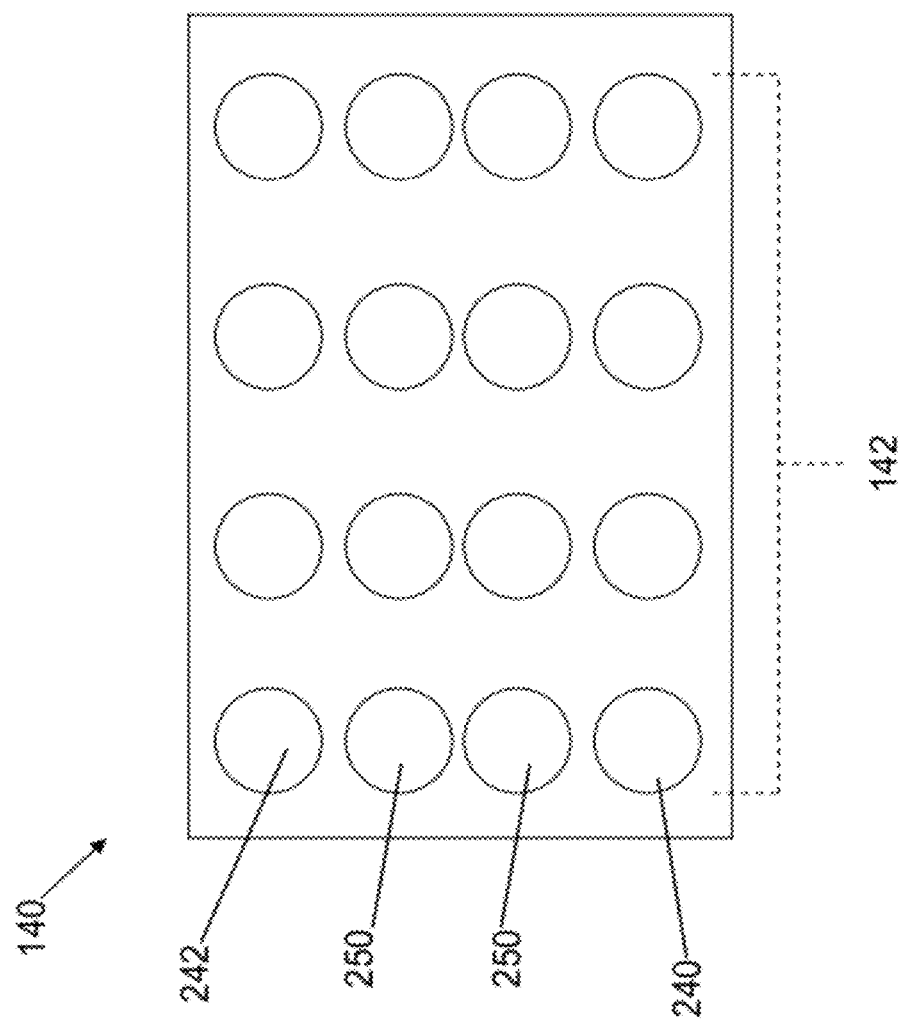
FIG. 3 shows an underside view of a glucose monitor according to one embodiment of the invention.
Figure 4:
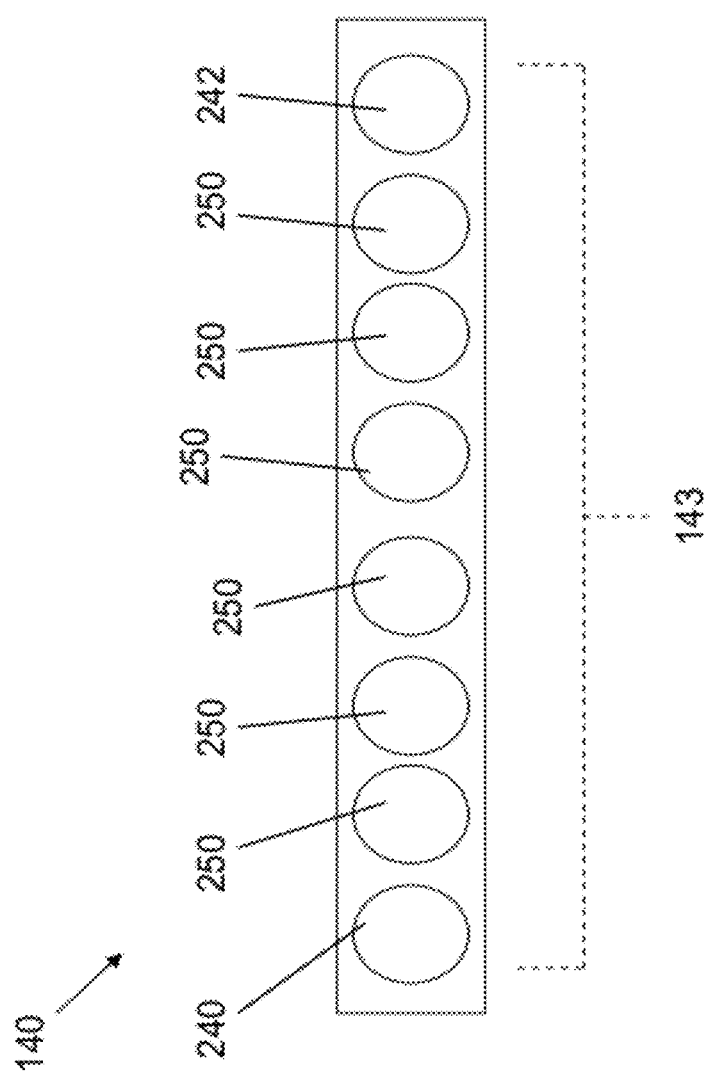
FIG. 4 shows an underside view of a glucose monitor according to another embodiment of the invention.
Figure 5:
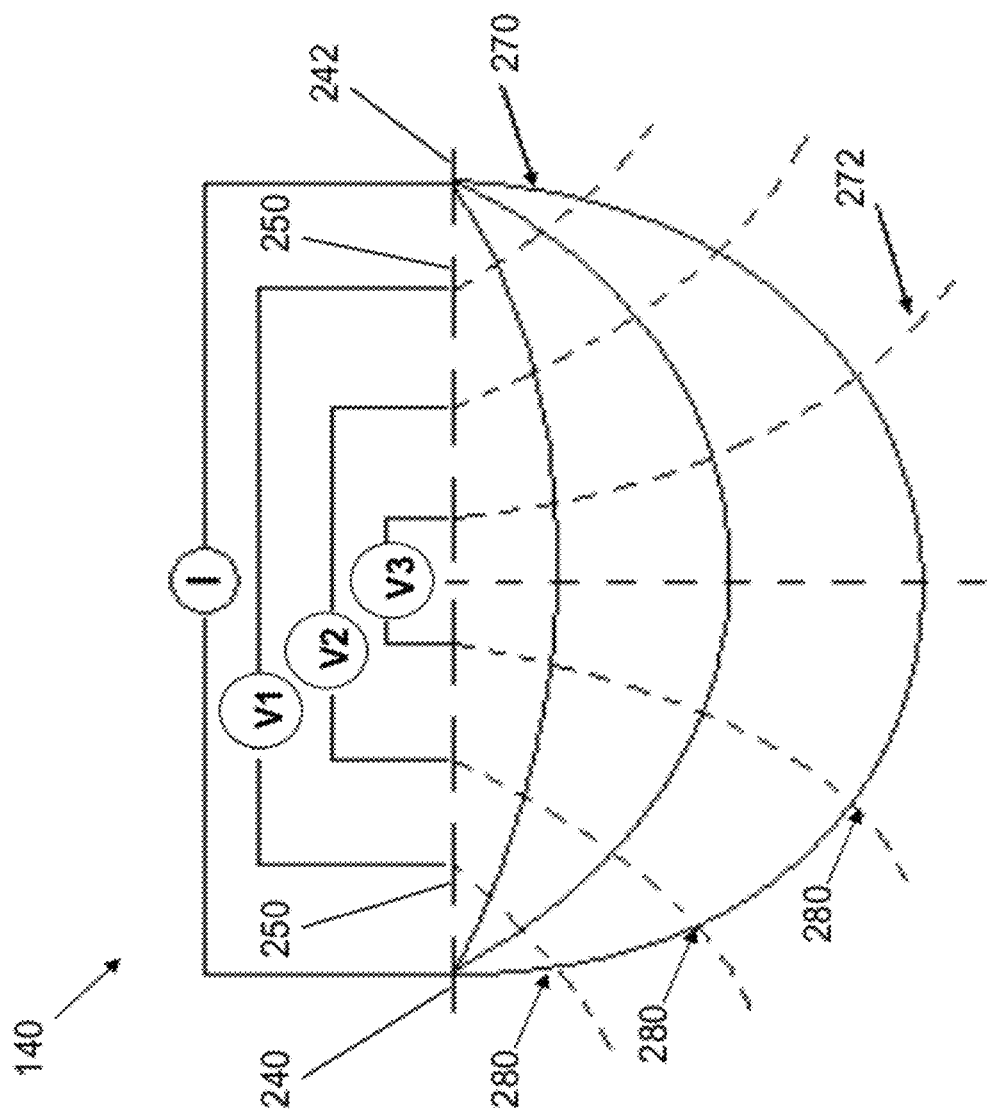
FIG. 5 shows a schematic diagram of a glucose monitor according to embodiments of the invention.
Figure 6:
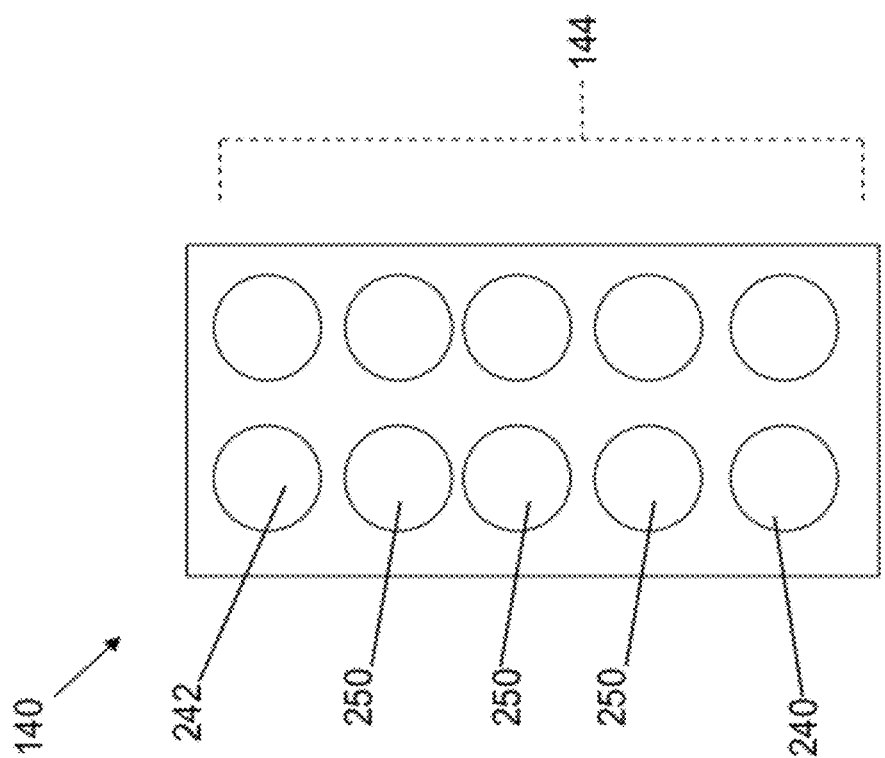
FIG. 6 shows an underside view of a glucose monitor according to an alternative embodiment of the invention.

Sensor array 142 will now be explained with reference to FIGS. 3-6, which show examples of sensor array 142, 143, 144 having a plurality of sensors 240, 242, 250. As shown in FIG. 3, sensor array 142 may include current transmitting sensors 240, 242, current receiving sensors 240, 242, and voltage sensors 250. Operation of each of these elements is discussed herein. While shown and described in several configurations, arrangements of sensor array 142 and sensors 240, 242, 250 are merely illustrative. Current transmitting sensors 240, 242, current receiving sensors 240, 242, and voltage sensors 250 may be positioned in sensor array 142 in other arrangements than those shown in FIG. 3. For example, voltage sensors 250 may, for example, be positioned between current transmitting sensors 240, 242 and current receiving sensors 240, 242 in a linear arrangement (FIGS. 4-5). However, current transmitting sensors 240, 242 and current receiving sensors 240, 242 may, for example, be positioned between voltage sensors 250 in a linear arrangement. Further, sensor array 142 and sensors 240, 242, 250 may, for example, be configured in other arrangements such as circular or arced arrangements. FIGS. 4-6 show alternative embodiments of sensor array 142. As shown in FIG. 3, sensor array 142 includes sixteen sensors. However, sensor array 142 may contain fewer or greater numbers of sensors 240, 242, 250 than those shown. For example, sensor array 143 of FIG. 4 includes eight sensors 240, 242, 250, while sensor array 144 of FIG. 6 includes ten sensors 240, 242, 250. Sensor array 142 and sensors 240, 242, 250 may be formed of conductive materials including, for example, silver/silver chloride, platinum or carbon. However, sensor array 142 and sensors 240, 242, 250 may be formed of other conductive materials now known or later developed. In one embodiment, sensors 240, 242, 250 may be conventional electrodes capable of performing the functions described herein.

In any case, sensors 240, 242, 250 may be functionally interchanged on sensor array 142. Interchanging of sensors 240, 242, 250 may not require physical removal and replacement of sensors, but may be performed through reprogramming of sensor array 142 by glucose monitoring system 106. For example, sensor array 142 may be reprogrammed by a user via glucose monitoring system 106, to change sensor 242 from a current transmitting sensor into a current receiving sensor. Further, sensor array 142 may be reprogrammed by a user to change sensor 242 from a current transmitting sensor into a voltage sensor. This interchangeability will be further explained with reference to FIGS. 4-6.

Turning back to FIG. 2, and step S1, sensor array 142 may repeatedly measure plurality of electromagnetic impedance readings 144 from the epidermis layer and one of the dermis layer or subcutaneous layer of a patient until a difference between the readings exceeds a threshold. Plurality of electromagnetic impedance readings 144 from the epidermis layer may be measured substantially simultaneously with respect to one another, or may be measured consecutively. Further, plurality of electromagnetic impedance readings 144 from one of the dermis layer or subcutaneous layer may be measured substantially simultaneously with respect to one another, or may be measured consecutively. Additionally, plurality of electromagnetic impedance readings 144 from the epidermis and the dermis or subcutaneous may be measured substantially simultaneously with respect to one another. In one embodiment, plurality of electromagnetic impedance readings 144 from the epidermis and one of the dermis or subcutaneous layers may be measured within less than approximately six minutes of one another to ensure an accurate measure of the patient's glucose level. As is known in the art, the typical glucose cycle (cellular oscillations of glucose metabolism) of a human patient is approximately two to six minutes long. In some patients, this glucose cycle may be as long as ten minutes. In this case, plurality of electromagnetic impedance readings 144 may be measured within approximately ten minutes of one another. Measuring plurality of electromagnetic impedance readings 144 within one glucose cycle of a patient provides an accurate measure of a glucose level of that patient.

It is further understood that electromagnetic impedance readings 144 from the epidermis layer and one of the dermis or subcutaneous layer are used as "shallow" and "deep" readings, respectively. As used herein, the epidermis layer refers to the outer layer of the skin covering the exterior body surface of the patient. The dermis layer refers to a layer of skin below the epidermis that includes the papillary dermis and reticular dermis. The dermis layer also includes small blood vessels (capillary bad) and specialized cells, including eccrine (sweat) glands and sebaceous (oil) glands. The subcutaneous layer refers to a layer of skin beneath the epidermis and dermis layer that includes fatty tissue and large blood vessels. While the dermis and subcutaneous layers are described herein with reference to "deep" readings, it is understood that other layers of tissue below the epidermis may provide sufficiently "deep" readings as well.

As described with reference to FIG. 4, sensor array 143 may pass a plurality of alternating current signals through different layers of the patient. In one embodiment, a signal generator (not shown) may generate an electromagnetic signal and transmit that signal to sensor array 143. In this case, signal generator may be any conventional signal generator known in the art. In another embodiment, sensor array 143 may include a signal generator which produces an electromagnetic signal. In another embodiment, current transmitting sensor 240 may include, or be electrically coupled to, a conventional signal generator capable of producing an electromagnetic signal. In any case, current transmitting sensor 240 and current receiving sensor 242 create an electromagnetic circuit which uses the layer(s) of the patient as a conducting medium. As described herein, current transmitting sensor 240 may produce an alternating current signal which is transmitted through the layer(s) of the patient, and received by current receiving sensor 242. The alternating-current signal may be within a frequency range that maximizes extraction of a glucose reading from the patient. This frequency may range from about 100 Hz to about 10 MHz. When a signal is transmitted through a layer of the patient, a voltage differential may be measured within that layer. Voltage sensors 250 determine this voltage differential within the layer of the patient, and glucose monitor 140 is capable of transmitting this voltage differential to glucose monitoring system 106. It is understood that the number of voltage sensors 250 is merely illustrative, and that as many as 12 voltage sensors may be located in sensor array 143 or other sensor arrays 142, 144.

Turning to FIG. 5, a circuit diagram of glucose monitor 140 having sensor array 143 of FIG. 4 is shown. FIG. 5 includes current transmitting sensor 240, current receiving sensor 242, and six (6) voltage sensors 250 (some labels omitted). The alternating current signal transmitted between current transmitting sensor 240 and current receiving sensor 242 is indicated by current distribution lines 270. Equipotential surface lines 272 are also shown, indicating surfaces of constant scalar potential (voltage). Further, current measurement line ("I") and voltage measurement lines "V1", "V2" and "V3" are shown, illustrating that current and voltages may be measured across sensors 240, 242, 250, respectively. As shown in FIG. 4, voltage sensors 250 are located between current transmitting sensors 240, 242 and current receiving sensors 240, 242 in a linear arrangement. Three "sets" of voltage sensors 250 are illustrated by voltage measurements V1, V2 and V3. The relationship between locations of sensors 240, 242, 250, along with properties of the underlying tissue (or, "material under test"), dictate the depth at which a voltage may be measured. In this illustrative example, intersections 280 may demonstrate the different depths at which a voltage can be measured by showing where equipotential surface lines 272 intersect current distribution lines 270. Intersections 280 indicate that voltage sensors 250 farthest from current transmitting sensor 240 and current sensing sensor 242 are able to read voltage levels in the deepest tissue layers. In this case, V1 may represent a voltage reading across the epidermis layer of a patient. V2 represents a deeper reading than V1, and may measure data about the dermis layer of the patient. V3 represents a deeper reading than V2, and may measure data about the subcutaneous layers of the patient. As is understood from FIG. 5, interchangeability of sensors 240, 242, 250 may allow for measurements of different tissue layers through manipulation of sensor types.

FIG. 6 shows another alternative embodiment of glucose monitor 140 having sensor array 144. In this embodiment, two columns, each containing 5 sensors 240, 242, 250 are shown. Each column may include current transmitting sensor 240, 242, current receiving sensor 240, 242, and three voltage sensors 250. Voltage sensors 250 may be located between current transmitting sensor 240, 242 and current receiving sensor 240, 242 in a linear arrangement. Glucose monitor 140 may measure electromagnetic impedance readings 144 at different layers (i.e., epidermis, dermis, subcutaneous) using different combinations of voltage sensors 250 within a row or between columns. As similarly described with reference to FIGS. 3-5, types of sensors 240, 242, 250 in sensor array 144 may be interchanged within or between columns to allow for measurements of different tissue layers.

Returning to FIG. 2, in step S2, comparator 110 compares the difference between the electromagnetic impedance readings to a threshold difference. The threshold difference may be, for example, a single impedance value or an impedance range which establishes that the difference (in impedance value) contains enough information about the deep reading to determine a glucose level of the patient. The threshold difference may be determined by the location of sensors 240, 242, 250 used to measure electromagnetic impedance readings, by the signal-to-noise ratio of the electronic components (not shown) within glucose monitor 140, and by the characteristics of the material under test (patient tissue). In order to compensate for fluctuations in electromagnetic impedance readings 144 from the epidermis layer, the difference must be great enough to provide sufficient information about the glucose level at one of the dermis layer or the subcutaneous layer.

In step S3A, in response to the difference being less than the threshold difference, the measuring and comparing steps are repeated until the difference is greater than the threshold difference. While described herein as a "difference", this value may be a complex mathematical value and/or a complex equation. The difference may be calculated using an iterative process of measuring readings 144 from different layers of a patient and adjusting subsequent readings 144 based upon known relationships between layers. For example, in one embodiment, it is unknown if an initial alternating-current signal will penetrate beyond the epidermis layer of a patient. In this case, by adjusting locations of sensors 240, 242, 250 and frequency ranges, different electromagnetic impedance readings 144 may be obtained. From those different electromagnetic impedance readings 144 and the known relationships between a patient's skin layers, penetration of different layers may be determined. In another embodiment, the difference may be calculated using one or more mathematical evaluation techniques such as Nyquist or Neural Networks techniques. However, it is understood that any other known mathematical technique may be used as well.

Figure 7:
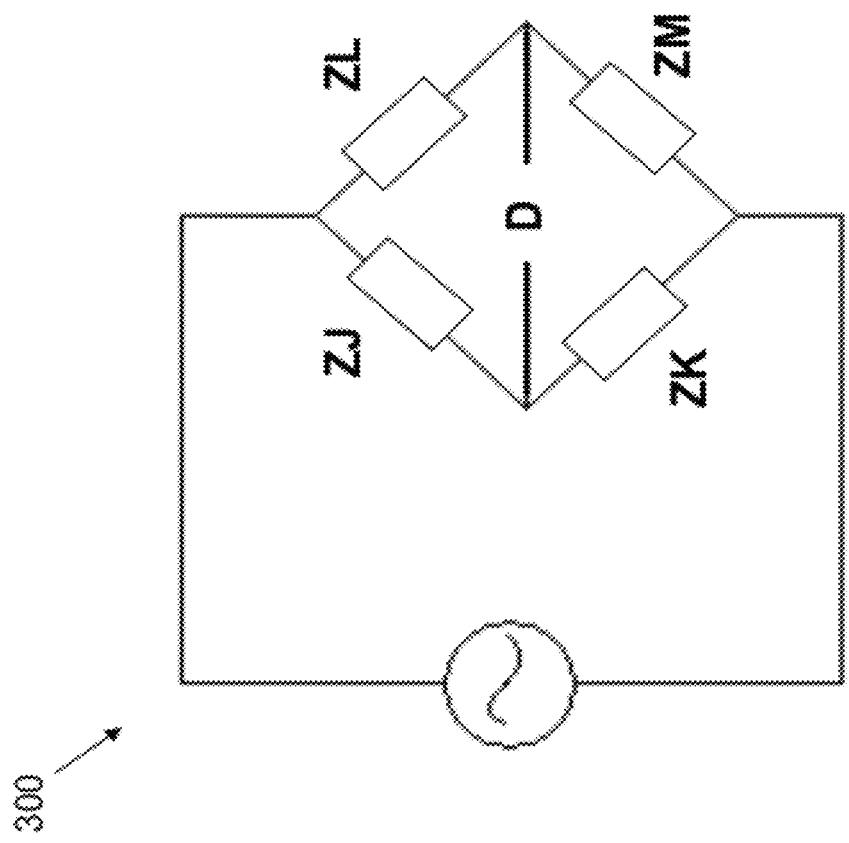
FIG. 7 shows an equivalent circuit model diagram according to embodiments of the invention.

In step S3, in response to the difference being at least equal to the threshold difference, calculator 124 calculates an impedance value representing the difference using an equivalent circuit model and individual adjustment factor data. The equivalent circuit model may resemble a traditional alternating current (AC) bridge circuit equation, whereby impedances of four elements of a circuit are balanced when a "zero" or null reading is measured at the output. In this case, the equivalent circuit model uses plurality of impedance readings 144 from the epidermis layer and plurality of impedance readings 144 from one of the dermis layer or subcutaneous layer as "elements" of the AC bridge. FIG. 7 shows an example of an AC circuit model 300 according to one embodiment of the invention. In this case, the balancing equation for the equivalent circuit model may be:

$$D=((ZK/(ZJ+ZK))-(ZM/(ZL+ZM))$$

In the example of FIG. 7, ZJ is a first electromagnetic impedance reading from the epidermis layer, ZK is a first electromagnetic impedance reading from the one of the dermis layer or the subcutaneous layer, ZM is a second electromagnetic impedance reading from the epidermis layer, ZL is a second electromagnetic impedance reading from the one of the dermis layer or the subcutaneous layer, and D is the impedance value representing the difference. Particular sensors 240, 242, 250 within sensor array 140 used to obtain readings ZJ, ZM, ZK and ZL are chosen by comparator 110. Using this equation, calculator 124 may calculate the impedance value representing the difference. It is understood that the impedance value representing the difference between readings from the epidermis and one of the dermis or subcutaneous layers is an impedance value representing one of the dermis or subcutaneous layers. Therefore, the impedance value D includes information about the dermis or subcutaneous layer of the patient, and may be used to determine a glucose level of that patient, as described herein.

In step S4, determinator 126 determines a glucose level of the patient from the impedance value representing the difference and a glucose algorithm. The glucose algorithm may include electromagnetic impedance versus glucose level correlation information. For example, the glucose algorithm may be derived from empirical data gathered from patients and corresponding electromagnetic impedance values assigned to that empirical data. In this case, a plurality of patients may be tested via conventional glucose-testing techniques, such as the classic finger-stick approach (further described herein). The glucose-level determinations made through the conventional test may then be paired with electromagnetic impedance values and further testing may be performed to evaluate these pairings. Through this iterative process, a range of electromagnetic impedances may be correlated to a range of glucose levels for a particular patient profile. For example, a patient profile may be established for a group of patients, with one such example profile being: Caucasian women, between the ages of 45-50, weighing 120-130 pounds, with 15-18% body fat, etc. Where a patient falls within this profile, a glucose level of the patient may be determined using an impedance value representing the difference between readings (epidermis and dermis/subcutaneous) measured from the patient, and a glucose algorithm tailored to the patient's profile. In another embodiment, the glucose algorithm may be specifically tailored to one patient. In this case, the glucose algorithm may be derived from empirical data gathered only from the patient. In contrast to the plurality of electromagnetic impedance readings gathered in determining a glucose level of the patient, this empirical data (glucose-level data and electromagnetic impedance data) may be gathered over a period lasting longer than one glucose cycle of the patient. This patient-specific glucose algorithm may provide more accurate results in determining the patient's glucose level than a glucose algorithm for a general patient profile. In any case, determinator 126 determines a glucose level of the patient from the impedance value representing the difference and a glucose algorithm.

In optional step S5, calibrator 128 may calibrate sensor array 142 by comparing the glucose level of the patient to a known glucose level of the patient. The known glucose level of the patient may be obtained, for example, by a classic finger-stick approach. In this case, the patient's blood is taken by puncturing the skin of his/her fingertip, and collecting the blood, for example, in a vial. That blood may then be analyzed using traditional glucose measuring techniques to determine a glucose level. A finger-stick is only one example of a traditional method in which a known glucose level of the patient may be obtained. A known glucose level of the patient may be obtained in a variety of other manners known in the art. In any case, the known glucose level may then be compared to the glucose level determined by the glucose determinator 126. In the case that the known glucose level and the determined glucose level are not the same, calibrator 128 may calibrate glucose monitor 140 by making adjustments to sensor activity states and types. For example, in sensor array 143 of FIG. 4, calibrator 128 may provide instructions to glucose monitor 140 to convert a pair of voltage sensors 250 into a current transmitting sensor 240 and a current receiving sensor 242, respectively. Calibrator 128 may further provide instructions to glucose monitor 140 to use a distinct pair of voltage sensors 250 for obtaining electromagnetic impedance data about the patient. Calibration may be performed without a restart of glucose monitoring system 106, and a calibration queue or wait time may be indicated on a portion of display 342 (FIG. 8).

It is understood that calibrating of sensor array 142 may be performed separately from the steps described herein. For example, calibrating of sensor array 142 may be performed before the measuring step S1, and may be based on a patient profile (which may include data representative of a physiological characteristic of the patient). This patient profile may include information such as the patient's body weight, body fat percentage, age, sex, etc. The patient profile may further include patient-specific information such as, for example, skin thickness information and testing location information (e.g., forearm area, wrist, back, etc.). Using a patient profile, calibrator 128 may provide instructions to glucose monitor 140 to use one or more voltage sensors and one or more sets of current transmitting sensors 240 and current receiving sensors 242 for obtaining electromagnetic impedance data about the patient.

Figure 8:
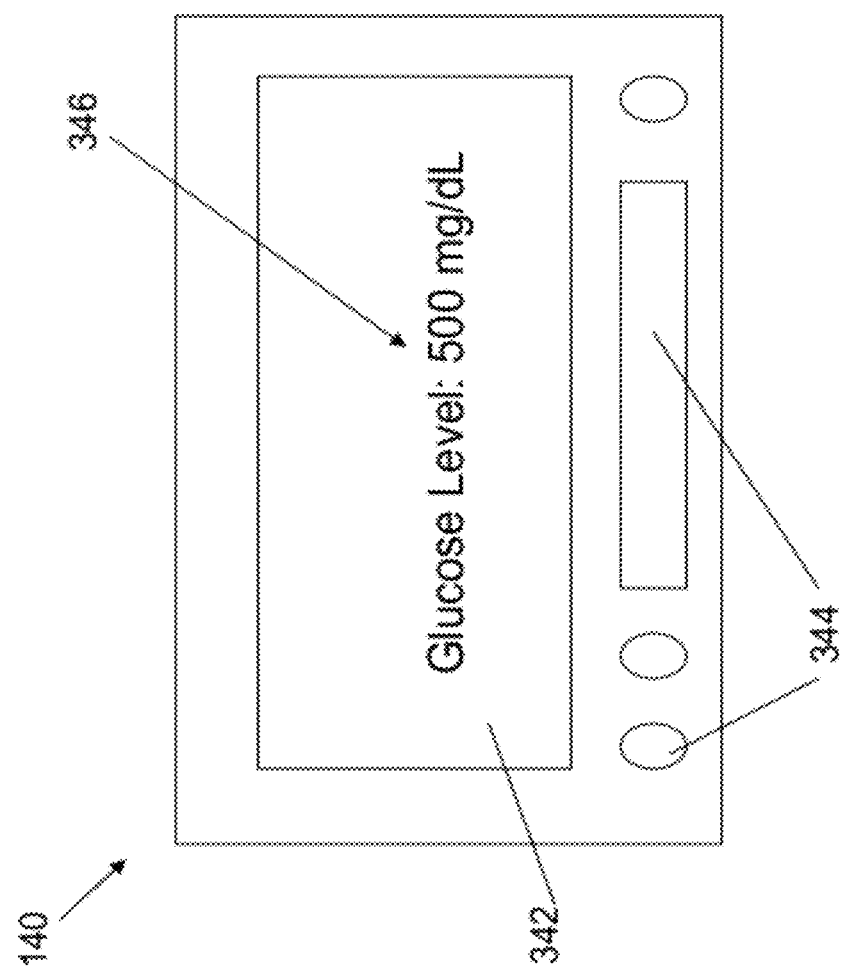
FIG. 8 shows a top view of a glucose monitor according to an embodiment of the invention.

Turning to FIG. 8, a top view of glucose monitor 140 is shown. Glucose monitor 140 may include a display 342, and a plurality of controls 344. Display 342 may provide a glucose reading 346 ("Glucose Level: 500 mg/dL"), which is visible to the patient and others observing display 342. Glucose reading 346 may be provided in response to actuation of controls 344. In some cases, glucose reading 346 may include historical glucose data, which allows a patient to view glucose data over a plurality of time intervals. Further, glucose reading 346 may provide graphical representations of glucose data in response to actuation of controls 344. Additionally, glucose data may be stored and/or transferred to storage system 122 and/or computer device 104. It should also be understood that glucose monitor 140 and sensor arrays 142, 143, 144 may be at separate locations. For example, sensor arrays 142, 143, 144 may gather electromagnetic impedance readings 144 from the wrist, back, thigh, etc., of a patient and transmit electromagnetic impedance readings 144 to glucose monitor 140. Glucose monitor 140 may transmit electromagnetic impedance readings 144 to, for example, glucose monitoring system 106 using a hard-wired or wireless connection.

Figure 9:
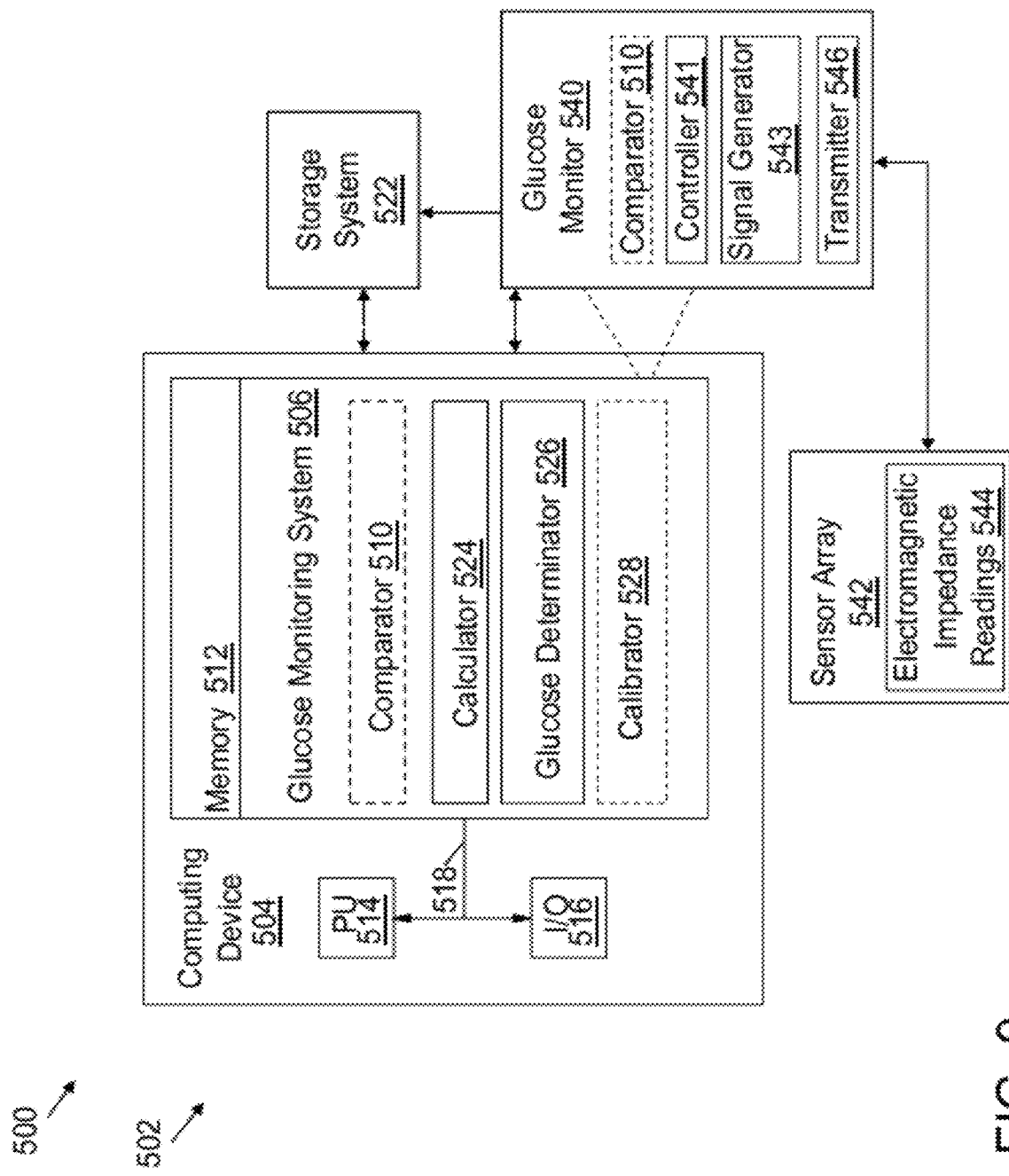
FIG. 9 shows a block diagram of an illustrative environment and computer infrastructure for implementing one embodiment of the invention.

FIG. 9 shows an illustrative environment 500 for monitoring a glucose level of a patient according to another embodiment of the invention. To this extent, environment 500 includes a computer infrastructure 502 that can perform the various processes described herein. In particular, computer infrastructure 502 is shown including a computing device 504 that comprises a glucose monitoring system 506, which enables computing device 504 to enable monitoring a glucose level of a patient by performing the steps described herein. It is understood that as compared with illustrative environment 100 of FIG. 1, commonly named components (e.g., memory, calculator, storage system, etc.) may function similarly as described herein and referenced in FIG. 1.

As shown in FIG. 9, glucose monitoring system 506 may include a comparator 510 (optionally), a calculator 524, a glucose determinator 526 and a calibrator 528 (optionally). Glucose monitoring system 506 is shown in communication with storage system 522, and/or Glucose monitor 540, via computing device 504. Glucose monitor 540 may include comparator 510 (optionally), a controller 541, a signal generator 543 and a transmitter 546. Glucose monitor 540 is shown in communication with sensor array 542, which may obtain electromagnetic impedance readings 544 from a patient (not shown).

In this embodiment, sensor array 542 may be a separate component from glucose monitor 540 and glucose monitoring system 506. For example, sensor array 542 may be a disposable array of electrodes, arranged in any configuration described herein. As described herein, sensor array 542 may non-invasively obtain electromagnetic impedance readings 544 from a body part of a patient. Sensor array 542 may be connected to glucose monitor 540 via hard-wired or wireless means. In any case, sensor array 542 is capable of exchanging signals with glucose monitor 540 and/or a patient. In one embodiment, controller 541 may instruct signal generator 543 to generate an electrical signal (e.g., an alternating current signal) and transmitter 546 to transmit the electrical signal to sensor array 542. Signal generator 543 and transmitter 546 may be any conventional signal generator and transmitter known in the art. In any case, after sensor array 542 receives the electrical signal from transmitter 546, sensor array 542 may measure a plurality of electromagnetic impedance readings 544 from a patient. Measuring of electromagnetic impedance readings 544 may be performed in any manner described herein or known in the art. Sensor array 542 may return electromagnetic impedance readings 544 to glucose monitor 540 via any conventional means (e.g., separate transmitter located on sensor array 542). However, in the case that sensor array 542 and glucose monitor 540 are hard-wired to one another, transmitter 546 and the transmitter located on sensor array 542 may not be necessary for exchanging electrical signals. In any case, sensor array 542 may transmit electromagnetic impedance readings 544 to glucose monitor 540.

In one embodiment, comparator 510 is a component within glucose monitor 540. In this case, comparator 510 may function substantially similarly to comparator 110 of FIG. 1. Upon instruction from controller 541, comparator 510 compares the electromagnetic impedance readings 544 to determine if a difference between the readings 544 exceeds a threshold. If the difference exceeds the threshold, controller 541 may instruct transmitter 546 to transmit the electromagnetic impedance readings 544 representing the difference to glucose monitoring system 506. If the difference does not exceed the threshold, controller 541 may instruct signal generator 543 and transmitter 546 (optionally) to send additional electrical signals to sensor array 542 for measuring additional electromagnetic impedance readings 544. Controller 541 and comparator 510 may repeat this process until a difference between the readings 544 exceeds a threshold difference.

Glucose monitor 540 and glucose monitoring system 506 may be connected by hard-wired or wireless means. In one embodiment, where glucose monitor 540 is wirelessly connected to glucose monitoring system 506, transmitter 546 may transmit electromagnetic impedance readings 544 to glucose monitoring system 506 using radio frequency (RF) wireless transmission. In any case, glucose monitor 540 transmits electromagnetic impedance readings 544 to glucose monitoring system 506, which may function substantially similarly to glucose monitoring system 106 of FIG. 1.

In an alternative embodiment, comparator 510 may be a component in glucose monitoring system 506 (similarly shown and described with respect to glucose monitoring system 106 of FIG. 1). In this case, comparator 510 may communicate with glucose monitor 540, and specifically, with controller 541, in order to obtain electromagnetic impedance readings 544 that represent a threshold difference. Once obtained, these readings 544 may be processed as described with reference to FIG. 1 (e.g., using calculator 524, glucose determinator 526, etc.).

In another alternative embodiment (shown in phantom), glucose monitor 540 and its components may be incorporated into glucose monitoring system 506 (and/or computing device 504). In this case, illustrative environment 500 includes two components: computing device 504 and sensor array 542. Here, computing device 504 may be either hard-wired or wirelessly connected to sensor array 542, and the functions of glucose monitor 540 may all be performed by glucose monitoring system 506. In any case, glucose monitoring system 506, glucose monitor 540 and sensor array 542 provide for non-invasive monitoring of a patient's blood metabolite (e.g., glucose) level.

EXAMPLES

The following provides particular examples of embodiments described herein.

Example 1

Identification of Tissue Layers

Figure 10:
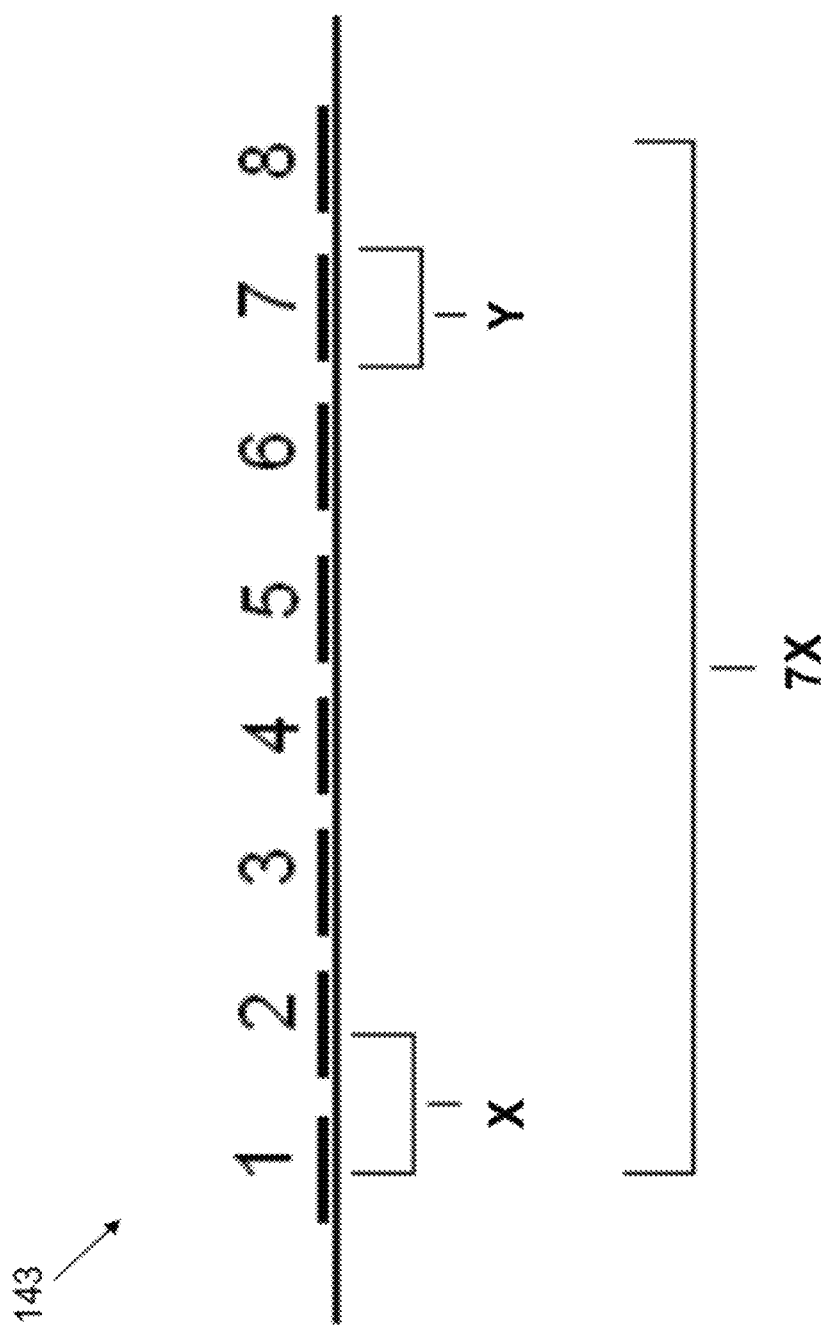
FIG. 10 shows a schematic side view of a sensor array according to an embodiment of the invention.

The following is an illustrative example of experimental results obtained through the use of glucose monitor 140 having sensor array 143 of FIG. 4. All sensors used in this experiment were disposable BIOPAC® electrodes (BIOPAC® is a registered trademark of BIOPAC Systems Inc., Goleta, Calif.), each electrode having a diameter of 10.5 mm. FIG. 10 shows a schematic side-view of sensor array 143, as used in this experiment. As described herein, each electrode in sensor array 143 was assigned a number (1-8). Sensor array 143 was configured such that the distance between electrodes (center-to-center) was X and the distance from the center of electrode 1 to the center of electrode 8 was 7X (equal spacing between electrodes). In this example, measurements were obtained using sets of four electrodes, including one current transmitting electrode, one current receiving electrode and two voltage sensing electrodes. FIG. 11 shows a table illustrating nine test patterns (A through I), used during the experiment. As illustrated in FIG. 11, entry "A" denotes a current transmitting electrode, entry "B" denotes a current receiving electrode, and entries "M" and "N" denote voltage sensing electrodes. It is understood that current transmitting electrode "A" may be interchanged with current receiving electrode "B" in all configurations. As such, for the purposes of this explanation, both current transmitting electrode "A" and current receiving electrode "B" will be referred to as "current carrying electrodes A and B."

This experiment was performed on a layer of animal skin tissue and a plurality of layers of animal muscle tissue. Initially, the animal skin tissue was placed over the plurality of layers of animal muscle tissue and subjected to an electrical current. At differing points during this experiment, the animal skin tissue was placed between animal muscle tissue layers to determine depth of measurement. An Agilent HP 4192A Impedance Analyzer ("impedance analyzer") was used to measure the potential difference between the two voltage sensing electrodes (M and N) while the electrical current was transmitted between current carrying electrodes A and B. For the purposes of this experiment, a limited number of electrode patterns were selected. As such, two conditions were set: 1) current carrying electrodes A and B were to be outside voltage detecting electrodes M and N; and 2) the distance between electrodes A and M were to be equal to the distance between electrodes N and B in every configuration. Given these conditions nine possible patterns (A through I) were used (FIG. 11). Using the impedance analyzer at a frequency of 100 kHz, electromagnetic impedance data was collected with each electrode pattern (A through I) for each configuration of skin tissue and muscle tissue. These tests indicated that the depth at which a measurement may be obtained depends on the resistivity (i.e., 1/conductivity) of the material under test (i.e., skin tissue) as well as the configuration of the four active electrodes used to complete the measurement. It is known that when the distance between all electrodes (A, B, M, and N) is equal, the depth of measurement is equal to the distance between electrodes. Using the sensor array 143 of FIG. 4, there are two instances when D(A-M)=D(N-B)=D(M-N). This occurs in patterns A and E of FIG. 10. In pattern A, D(A-M)=D(N-B)=D(M-N)=11.75 mm and in pattern E, D(A-M)=D(N-B)=D(M-N)=23.5 mm. Using this theory, electrode pattern A would determine characteristics of tissue at a depth of 11.75 mm and electrode pattern E would determine characteristics of tissue at a depth of 23.5 mm. However, conducting this experiment using patterns A and E obtained slightly different results. Electrode pattern A was able to measure a depth of 9.5 mm, while electrode pattern E was able to measure a depth of 18.75 mm. These are 19% and 20% deviations, respectively. These deviations were later used to calibrate sensor array 143 and determine different measurement depths based upon the material under test and the electrodes used in sensor array 143.

Example 2

Tissue Volume Removal

Figure 12:
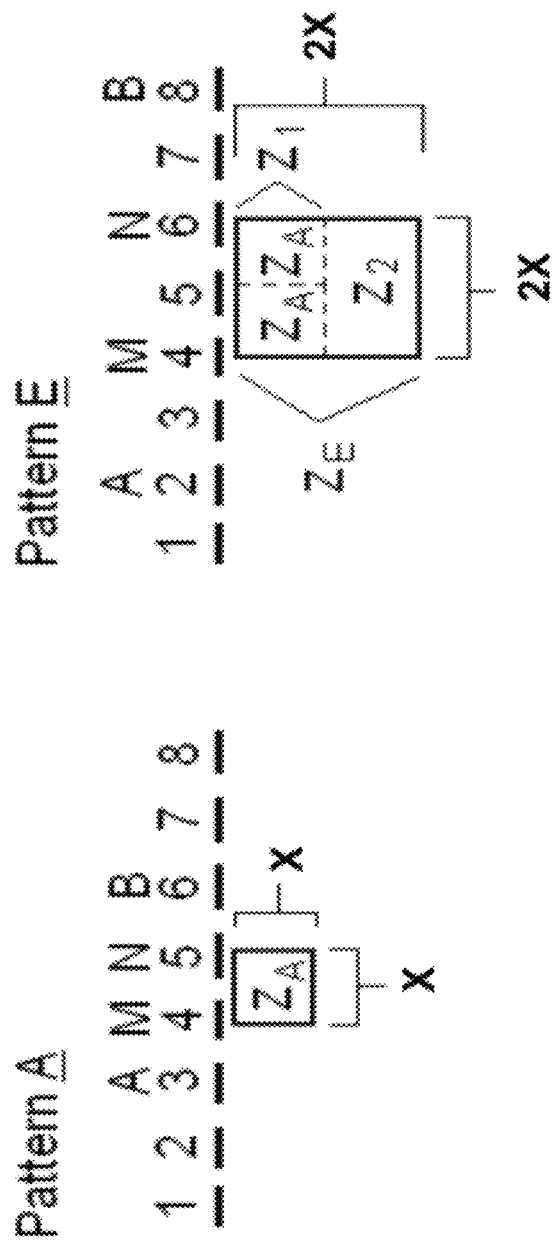
FIG. 12 shows schematic side views of a sensor array corresponding to the test patterns of FIG. 11.

FIG. 12 shows a conceptual model of the measured tissue volumes and their measured impedances. In this model, $Z_A$ represents the impedance measurement and volume measured of pattern A and $Z_E$ represents the impedance measurement and volume measured of pattern E. In this test, the distance between electrodes in pattern E is twice that the distance between electrodes in pattern A (2X versus X). Therefore, when removing the effect of $Z_A$ from $Z_E$ (determining the difference between $Z_A$ and $Z_E$), Z1 is equal to $Z_A$ in series with $Z_A$, thus Z1=$Z_A$+$Z_A$ (Equation 1 below). $Z_E$ is the parallel combination of Z1 and Z2, whereby the parallel combination equation is, $Z_E$=(Z1Z2)/(Z1+Z2). Substituting for Z1 results in, $Z_E$=($Z_A$+$Z_A$)*Z2/(($Z_A$+$Z_A$)+Z2), where Z1 is the impedance value of the tissue from the surface to a depth of X and Z2 is the impedance value of the tissue from a depth of X to a depth of 2X. In one test, X was equal to approximately 11.75 millimeters (mm). As the goal of the tissue volume removal was to remove the effect of Z1 from $Z_E$, Equation 2 was derived from the equation for $Z_E$ (above), solving for Z2.

$$Z_1 = Z_A + Z_A \quad \text{(Equation 1)}$$

$$Z_2 = \frac{Z_1 Z_E}{Z_1 - Z_E} \quad \text{(Equation 2)}$$

To confirm the model, a second test was performed, this time concentrating on patterns A and E and using only animal muscle tissue having an average thickness of 24.61 mm. $Z_A$ and $Z_E$ were measured and Z1 and Z2 were calculated using Equations 1 and 2 described above. These magnitude and phase values are displayed in the table of FIG. 13. These magnitude and phase values help characterize results when only measuring muscle tissue. As shown in FIG. 13, the muscle tissue limits are: Z1=180Ω and 0.03°, Z2=437Ω and −1.03°. Therefore, when Z1 and Z2 are greater than 180Ω and 437Ω, respectively, a combination of skin and muscle are being measured. As Z1 and Z2 approached these limits, it was understood that Z1 and Z2 were not able to differentiate between muscle and skin tissue.

Example 3

Tissue Volume Differentiation

Further tests were performed to determine differences between readings from the epidermis layer and one of a dermis or subcutaneous layer of a patient. Using sensor array 143, electromagnetic impedance readings were measured from a standard sodium chloride solution of 140 mmol/L. Given a homogenous volume of sodium chloride solution, the relationships between the volumes measured by various electrode pairs (FIG. 11) at a single frequency were empirically derived, whereby:

$$Z_I = k_{IG} Z_G = k_{IC} Z_C \quad \text{(Equation 3)}$$

$$Z_G = k_{GC} Z_C \quad \text{(Equation 4)}$$

Where Z is the impedance of the patterns measured (I, G, C) and $k_{IG}$, $k_{IC}$ and $k_{GC}$ were calculated using the standard sodium chloride solution of 140 mmol/L. To test whether these empirically derived relationships hold true for animal tissues, two tests were completed. Test A was conducted on animal muscle tissue having a thickness of 35 mm, where the k values of the homogenous muscle tissue were consistent with the sodium chloride test (above). Test B was conducted with the a 1.35 mm thick piece of animal skin tissue placed over the same animal muscle tissue as Test A. Using Equation 3, the impedance $Z_I$ was "distinct" from impedances $Z_G$ and $Z_C$. Using Equation 4, the impedance $Z_G$ was not "distinct" from impedance $Z_C$. Electromagnetic impedances (Z) were considered "distinct" if the difference in measured electromagnetic impedances was greater than 10%. The measured electromagnetic impedance magnitude differences in Test B were:
  1) Percent difference between $Z_I$ and $Z_G$~29%,
  2) Percent difference between $Z_I$ and $Z_C$~37%, and
  3) Percent difference between $Z_G$ and $Z_C$~7%.

Example 4

Tissue Volume Differentiation and Removal (VDR)

Figure 14:
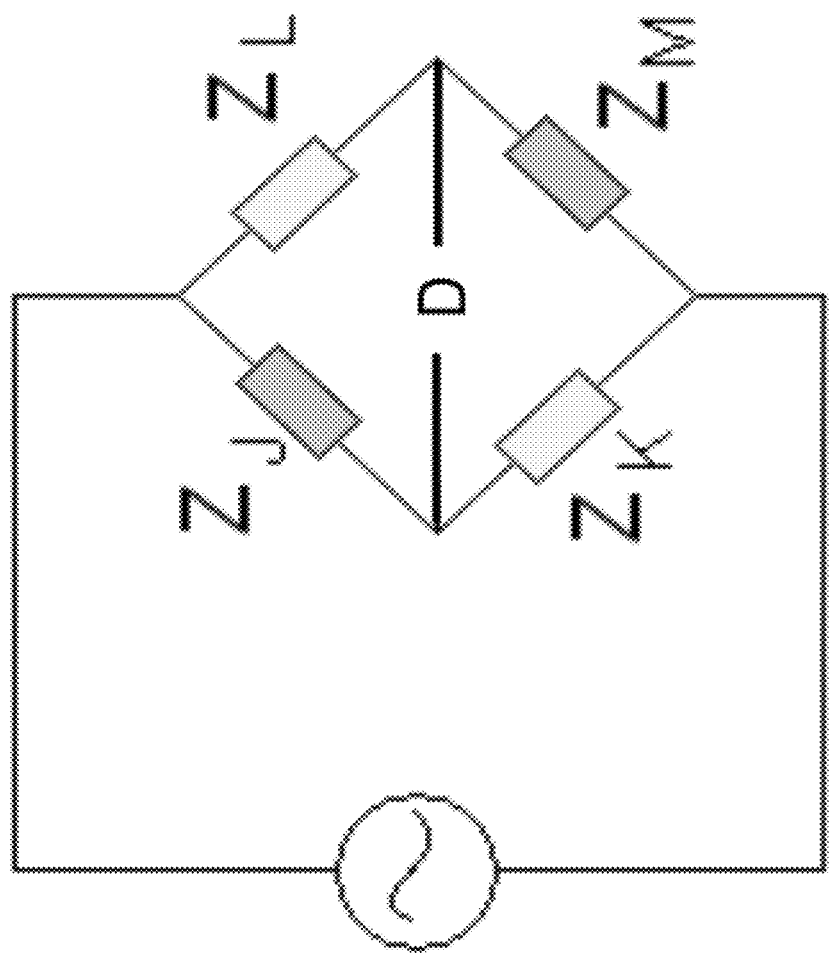
FIG. 14 shows an equivalent circuit model used during testing according to embodiments of the invention.

After determining that tissue volume differentiation and tissue volume removal were separately possible, it is possible to conduct volume differentiation and removal (VDR). This approach included measuring four electromagnetic impedance readings for each VDR approach. Specifically, two electromagnetic impedance readings may be measured from the upper volume (i.e., epidermis), while two electromagnetic impedance readings may be measured from the lower volume (i.e., dermis or subcutaneous). After identification of different tissue volumes, detailed above, four measurements may be used in an equivalent circuit model to calculate electromagnetic impedance values representing the difference between the volumes. In one embodiment, two of the four measurements are from the shallow volume (animal skin tissue), and another two are from the deep volume (animal skin tissue & animal muscle tissue). The equivalent circuit model is shown in FIG. 14, and resembles a traditional alternating current (AC) bridge model, whereby impedances are "balanced" across a zero or null reading (D). In FIG. 14, according to one embodiment, the electromagnetic impedances $Z_J$, $Z_M$ represent the shallow volume (animal skin tissue) and the electromagnetic impedances $Z_K$, $Z_L$ represent the total volume (i.e., shallow/deep volumes). From the AC bridge model, the following equivalent circuit model equation was derived:

$$D = \frac{Zk}{Zj+Zk} - \frac{Zm}{Zl+Zm} \quad \text{(Equation 5)}$$

Where "D" is the electromagnetic impedance value representing the difference between the shallow volume and the deep volume. By setting D to a zero value and measuring the electromagnetic impedance of the shallow volume and deep volume, ratios between the impedance values were determined. In another embodiment, ZJ, ZK, ZL and ZM may each represent electromagnetic impedances from more than one volume. For example, ZJ may represent electromagnetic impedance data about an epidermis layer and a dermis layer of a patient, while ZK may represent electromagnetic impedance data about the dermis layer and the epidermis layer of the patient. In this case, further differentiation between impedance readings (ZJ, ZK) is necessary to determine the difference D. In this case, impedance values ZJ and ZK can be divided into component parts (i.e., real and imaginary parts) and differentiation may be performed.

In another case, assumptions may be made about impedance values and their relationships to one another in order to facilitate determining the difference D. Looking at FIGS. 12-13, assumptions may be made about Z2, ZJ, and ZK in order to simplify determining the difference D. In this case, Z2 represents the difference D, while ZJ and ZK each represent some algebraic combination of ZA and ZE. Mathematically, these assumptions are as follows: D=Z2 (FIG. 11); ZJ=ZM; and ZK=ZL. Using these assumptions and substituting into Equation 5 results in:

$$Z2=((Z1*ZE)/(Z1-ZE)); \text{ and}$$

$$ZK=ZJ*(Z1*ZE+Z1-ZE)/(Z1-ZE-Z1*ZE).$$

While further modifications (assumptions and/or substitutions) are necessary in order to solve for ZK in the preceding equation, those modifications are within the level of skill of one in the art.

While shown and described herein as a method and system for monitoring blood metabolite levels (and more specifically, glucose levels) of a patient, it is understood that the disclosure further provides various alternative embodiments. That is, the disclosure can take the form of an entirely hardware embodiment, an entirely software embodiment or an embodiment containing both hardware and software elements. In a preferred embodiment, the disclosure is implemented in software, which includes but is not limited to firmware, resident software, microcode, etc. In one embodiment, the disclosure can take the form of a computer program product accessible from a computer-usable or computer-readable medium providing program code for use by or in connection with a computer or any instruction execution system, which when executed, enables a computer infrastructure to determine a glucose level of a patient. For the purposes of this description, a computer-usable or computer readable medium can be any apparatus that can contain, store or transport the program for use by or in connection with the instruction execution system, apparatus, or device. The medium can be an electronic, magnetic, optical, electromagnetic, infrared, or semiconductor system (or apparatus or device). Examples of a computer-readable medium include a semiconductor or solid state memory, such as storage system 122, magnetic tape, a removable computer diskette, a random access memory (RAM), a read-only memory (ROM), a tape, a rigid magnetic disk and an optical disk. Current examples of optical disks include compact disk-read only memory (CD-ROM), compact disk-read/write (CD-R/W) and DVD.

A data processing system suitable for storing and/or executing program code will include at least one processing unit 114 coupled directly or indirectly to memory elements through a system bus 118. The memory elements can include local memory, e.g., memory 112, employed during actual execution of the program code, bulk storage (e.g., storage system 122), and cache memories which provide temporary storage of at least some program code in order to reduce the number of times code must be retrieved from bulk storage during execution.

In another embodiment, the disclosure provides a method of generating a system for monitoring a glucose level of a patient. In this case, a computer infrastructure, such as computer infrastructure 102, 502 (FIGS. 1, 9), can be obtained (e.g., created, maintained, having made available to, etc.) and one or more systems for performing the process described herein can be obtained (e.g., created, purchased, used, modified, etc.) and deployed to the computer infrastructure. To this extent, the deployment of each system can comprise one or more of: (1) installing program code on a computing device, such as computing device 104, 504 (FIGS. 1, 9), from a computer-readable medium; (2) adding one or more computing devices to the computer infrastructure; and (3) incorporating and/or modifying one or more existing systems of the computer infrastructure, to enable the computer infrastructure to perform the process steps of the disclosure.

In still another embodiment, the disclosure provides a business method that performs the process described herein on a subscription, advertising, and/or fee basis. That is, a service provider, such as an application service provider, could offer to determine a glucose level of an animal as described herein. In this case, the service provider can manage (e.g., create, maintain, support, etc.) a computer infrastructure, such as computer infrastructure 102, 502 (FIGS. 1, 9), that performs the process described herein for one or more customers. In return, the service provider can receive payment from the customer(s) under a subscription and/or fee agreement, receive payment from the sale of advertising to one or more third parties, and/or the like.

As used herein, it is understood that the terms "program code" and "computer program code" are synonymous and mean any expression, in any language, code or notation, of a set of instructions that cause a computing device having an information processing capability to perform a particular function either directly or after any combination of the following: (a) conversion to another language, code or notation; (b) reproduction in a different material form; and/or (c) decompression. To this extent, program code can be embodied as one or more types of program products, such as an application/software program, component software/a library of functions, an operating system, a basic I/O system/driver for a particular computing and/or I/O device, and the like.

The foregoing description of various aspects of the invention has been presented for purposes of illustration and description. It is not intended to be exhaustive or to limit the invention to the precise form disclosed, and obviously, many modifications and variations are possible. Such modifications and variations that may be apparent to a person skilled in the art are intended to be included within the scope of the invention as defined by the accompanying claims.

What is claimed is:

1. A method of determining a blood metabolite level of a patient, the method comprising:
repeatedly transmitting, using a sensor array, a plurality of electromagnetic signals into an epidermis layer of a patient and one of a dermis layer of the patient, or the dermis layer and a subcutaneous layer of the patient;
repeatedly obtaining a plurality of return electromagnetic impedance readings, using the sensor array, from: the epidermis layer of a patient and the one of the dermis layer or the dermis layer and the subcutaneous layer of the patient, until a difference between the transmitted electromagnetic signals and the return electromagnetic impedance readings exceeds a threshold, the threshold being equal to approximately a ten percent difference,
wherein exceeding the threshold indicates that the transmitted plurality of electromagnetic signals penetrated the at least one of the dermis layer, or the dermis layer and subcutaneous layer,
wherein the repeatedly transmitting of the plurality of electromagnetic signals and the repeatedly obtaining of the plurality of return electromagnetic impedance readings is performed within approximately ten minutes;
calculating, at a glucose monitoring system having a processing unit and a memory, an impedance value representing the difference between the transmitted electromagnetic signals and the return electromagnetic signals using an equivalent circuit model and individual adjustment factor data representative of a physiological characteristic of the patient; and
determining a blood metabolite level of the patient from the impedance value and a blood metabolite level algorithm, the blood metabolite level algorithm including blood metabolite level data versus electromagnetic impedance data value correspondence.

2. The method of claim 1, further comprising: calibrating the sensor array based on the determined blood metabolite level of the patient and a known blood metabolite level of the patient obtained independently of the determined blood metabolite level of the patient.

3. The method of claim 1, wherein the blood metabolite level is a one of a glucose level, an electrolyte level or an analyte level.

4. The method of claim 1, wherein the individual adjustment factor data includes information about at least one of: a weight of the patient, a sex of the patient, a body fat percentage of the patient, a heart rate of the patient, an age of a patient, and a race of a patient.

5. The method of claim 1, wherein the sensor array contains a planar array of equally spaced electrodes.

6. The method of claim 1, wherein the equivalent circuit model includes an equivalent circuit equation including:

$$D=((ZK/(ZJ+ZK))-(ZM/(ZM+ZL))$$

where ZJ is a first electromagnetic impedance reading from the epidermis layer, ZM is a second electromagnetic impedance reading from the epidermis layer, ZK is a first electromagnetic impedance reading from the one of the dermis layer or the dermis layer and the subcutaneous layer, ZL is a second electromagnetic impedance reading from the one of the dermis layer or the dermis layer and the subcutaneous layer, and D is the impedance value representing the difference.

7. A monitoring system for at least one of a glucose level, an electrolyte level or an analyte level, the monitoring system comprising:
a sensor array for repeatedly transmitting a plurality of electromagnetic signals into an epidermis layer of a patient and one of a dermis layer of the patient, or the dermis layer and a subcutaneous layer of the patient;
repeatedly obtaining a plurality of return electromagnetic impedance readings from: the epidermis layer of a patient and the one of the dermis layer or the dermis layer and the subcutaneous layer of the patient, until a difference between the transmitted electromagnetic signals and the return electromagnetic impedance readings exceeds a threshold, the threshold being equal to approximately a ten percent difference,
wherein exceeding the threshold indicates that the transmitted plurality of electromagnetic signals penetrated the at least one of the dermis layer, or the dermis layer and subcutaneous layer,
wherein the repeatedly transmitting of the plurality of electromagnetic signals and the repeatedly obtaining of the plurality of return electromagnetic impedance readings is performed within approximately ten minutes;
a calculator for calculating an impedance value representing the difference between the transmitted electromagnetic signals and the return electromagnetic signals using an equivalent circuit model and individual adjustment factor data representative of a physiological characteristic of the patient; and
a determinator for determining the at least one of the glucose level, the electrolyte level or the analyte level of the patient from the impedance value and at least one of a glucose algorithm, an electrolyte algorithm or an analyte algorithm.

8. The monitoring system of claim 7, further comprising a signal generator for generating electromagnetic signals and transmitting the electromagnetic signals to the sensor array.

9. The monitoring system of claim 8, further comprising a signal analyzer for analyzing the electromagnetic signals and generating the electromagnetic impedance readings.

10. The monitoring system of claim 7, wherein the electromagnetic impedance readings are obtained at a frequency between approximately 10 Hz and 10 MHz.

11. The monitoring system of claim 7, wherein the sensor array contains at least seven sensors.

12. The monitoring system of claim 11, wherein the at least seven sensors are arranged in a substantially linear arrangement.

13. The monitoring system of claim 7, wherein the sensor array includes a current transmitting electrode, a current sensing electrode, and two voltage sensing electrodes positioned on the epidermis layer of the patient in a linear arrangement.

14. A program product stored on a non-transitory computer readable medium, which when executed by a computer, causes the computer to perform the following:

instructs a sensor array to repeatedly transmit a plurality of electromagnetic signals into an epidermis layer of a patient and one of a dermis layer of the patient, or the dermis layer and a subcutaneous layer of the patient;

determines a blood metabolite level of a patient based on a plurality of repeatedly obtained return electromagnetic impedance readings collected from the epidermis layer of the patient and the one of the dermis layer, or the dermis layer and the subcutaneous layer of the patient within approximately ten minutes, the plurality of electromagnetic signals being repeatedly transmitted and the plurality of return electromagnetic readings being repeatedly obtained until a difference between the plurality of transmitted electromagnetic signals and the plurality of obtained return electromagnetic readings exceeds a threshold equal to approximately a ten percent difference, wherein exceeding the threshold indicates that the transmitted plurality of electromagnetic signals penetrated the at least one of the dermis layer, or the dermis layer and subcutaneous layer; and provides instructions for calibrating the sensor array based on the determined blood metabolite level of the patient and a known blood metabolite level of the patient obtained independently of the determined blood metabolite level of the patient.

15. The program product of claim 14, wherein the blood metabolite level is one of a glucose level of the patient, an electrolyte level of the patient or an analyte level of the patient.

16. The monitoring system of claim 13, wherein the current transmitting electrode, the current sensing electrode and the two voltage sensing electrodes are spaced equally from one another within the sensor array.

17. The method of claim 1, wherein in response to determining that the difference between the transmitted electromagnetic signals and the return electromagnetic impedance readings does not exceed the threshold, repeating the transmitting of the plurality of electromagnetic signals and the obtaining of the plurality of return electromagnetic impedance readings for approximately ten minutes, and stopping.

18. The monitoring system of claim 7, wherein in response to determining that the difference between the transmitted electromagnetic signals and the return electromagnetic impedance readings does not exceed the threshold, repeating the transmitting of the plurality of electromagnetic signals and the obtaining of the plurality of return electromagnetic impedance readings for approximately ten minutes, and stopping.

19. The program product of claim 14, wherein in response to determining that the difference between the transmitted electromagnetic signals and the return electromagnetic impedance readings does not exceed the threshold, repeating the transmitting of the plurality of electromagnetic signals and the obtaining of the plurality of return electromagnetic impedance readings for approximately ten minutes, and stopping.

* * * * *